US005800422A

United States Patent [19]

Dong et al.

[11] Patent Number: 5,800,422

[45] Date of Patent: Sep. 1, 1998

[54] OSMOTIC DEVICE WITH DELAYED ACTIVATION OF DRUG DELIVERY AND COMPLETE DRUG RELEASE

[75] Inventors: Liang C. Dong, Sunnyvale; Patrick S.-L. Wong, Palo Alto; Si-Hong A. Yum, Daly City; Lawrence G. Hamel, Mountain View; Michael H. Dealey, San Francisco, all of Calif.

[73] Assignee: Alza Corporation, Palo Alto, Calif.

[21] Appl. No.: 700,323

[22] Filed: Aug. 8, 1996

Related U.S. Application Data

[63] Continuation of Ser. No. 459,387, Jun. 2, 1995, abandoned.

[51] Int. Cl.[6] .......... A61K 9/22

[52] U.S. Cl. .......... 604/892.1; 424/453

[58] Field of Search .......... 604/891.1, 892.1; 424/422–424, 473, 430, 451, 453, 462, 463

[56] References Cited

U.S. PATENT DOCUMENTS 3,845,770 11/1974 Theeuwes et al. .
3,865,108 2/1975 Hartop .
3,995,631 12/1976 Higuchi .
4,002,173 1/1977 Manning et al. .
4,034,756 7/1977 Higuchi et al. .
4,111,202 9/1978 Theeuwes .
4,207,893 6/1980 Michaels .
4,265,874 5/1981 Bonsen et al. .
4,320,759 3/1982 Theeuwes .
4,327,725 5/1982 Cortese et al. .
4,449,983 5/1984 Cortese et al. .
4,595,583 6/1986 Eckenhoff et al. .
4,612,008 9/1986 Wong et al. .
4,874,388 10/1989 Wong et al. .......... 604/891.1
5,198,229 3/1993 Wong et al. .......... 424/473
5,223,265 6/1993 Wong .
5,312,388 5/1994 Wong et al. .......... 604/892.1
5,312,390 5/1994 Wong .......... 604/892.1
5,324,280 6/1994 Wong et al. .......... 604/892.1
5,358,502 10/1994 Herbig et al. .......... 604/892.1
5,387,421 2/1995 Amidon et al. .......... 424/472

FOREIGN PATENT DOCUMENTS 0384642 8/1990 European Pat. Off. .

*Primary Examiner*—Wynn Wood Coggins
*Assistant Examiner*—A. T. Nguyen
*Attorney, Agent, or Firm*—John A. Dhuey; Steven F. Stone

[57] ABSTRACT

The present invention is directed to a fluid-imbibing drug delivery device which is useful for the initial delayed delivery of an active agent formulation to a fluid environment of use, the initial delay period to startup or activation of the device being of a predetermined length of time. The delivery of the agent formulation from the dispensing device is continued until essentially all of the active agent formulation is delivered as a result of the expansion of an expansion agent in the active agent delivery chamber.

16 Claims, 2 Drawing Sheets

OSMOTIC DEVICE WITH DELAYED ACTIVATION OF DRUG DELIVERY AND COMPLETE DRUG RELEASE

RELATED APPLICATIONS

This application is a continuation, of application Ser. No. 08/459,387, filed Jun. 2, 1995, now abandoned.

FIELD OF THE INVENTION

The present invention is related to the delayed delivery of an active agent followed by essentially complete delivery of the active agent. More particularly, it is related to osmotically-activated devices for essentially complete dispensing of active agents to a biological environment of use following an initial period of delay.

BACKGROUND OF THE INVENTION

Osmotic dispensing devices for delivery of therapeutically active agents are well known in the art. Such devices use an expansion means to deliver an agent to an environment of use over a period of hours, days or months. The expansion means absorbs liquid, expands, and acts to drive out the beneficial agent formulation from the interior of the device in a controlled, usually constant manner. The osmotic expansion means is used to controllably, usually relatively slowly, and over a period of time, deliver the agent.

Osmotic devices have also been described for prolonged and controlled delivery of one or more active agents where an initial delay of delivery is desired. U.S. Pat. No. 5,198,229 which is incorporated herein by reference, is directed to an osmotic device for delivery of an active agent to the upper gastrointestinal tract. The dispensing device comprises concentric housings that are in slidably telescoping arrangement with each other. A first expansion means imbibes fluid when placed in the stomach environment. This expansion means expands and pushes against a partition layer that in turn pushes against an active agent formulation. The active agent is delivered to the stomach environment through a small exit port in a controlled and continuous manner. After all the active agent has been delivered, the housings separate, the buoyancy chamber is exposed to the stomach environment, the density of the device increases, and the device sinks and exits out of the stomach.

U.S. Pat. No. 5,312,388 which is incorporated herein by reference, describes the use of slidably telescopic concentric housings in an osmotic device where delivery of more than one active agent is desired or where separate dosings of one active agent is desired. In a particular embodiment, initial rapid delivery of a particular active agent is followed by delayed delivery of the active agent. A loading dose of the active agent is dispensed as soon as the device enters the environment of use. Prolonged delivery is accomplished as a result of an expansion means that imbibes fluid and expands to separate the concentric housings. Upon separation, the active agent contained within the housings is dispensed.

U.S. Pat. No. 5,312,390 which is incorporated herein by reference, describes an osmotic device useful for the initially delayed delivery of an active agent. Slidably telescoping concentric housings separate following absorption of fluid through the housing. A fluid passage means is exposed to the fluid environment and the active agent is expelled in a controlled and continuous manner through an exit port at the end of the housing opposite the fluid passage means.

U.S. Pat. No. 5,358,502 describes an osmotic device with a semipermeable membrane with an agent that is pH sensitive and thus will degrade at a given pH. Degradation of the material will allow for release of the contents of the device.

As can be observed in the above-referenced patents, osmotic devices have been described that provide for an initial pulse of an active agent, that provide for prolonged delivery of an active agent, and that provide for delivery of more than one active agent. However, there remains a continuing need for improved methods and systems for delivering one or more active agents in a reliable and reproducible manner.

SUMMARY OF THE INVENTION

We have observed that devices such as those described above will open in a predictable manner but that the agent contained in the device may not always be completely released to the environment of use following the desired delay period. Accordingly, the present invention is directed to a fluid-imbibing dispensing device and a method for the essentially complete delivery of an active agent to a fluid environment of use following an initially delayed period of delivery of the agent.

In one aspect, the invention is directed to a fluid-imbibing delivery device formed of a first housing and a second housing. The housings are in reversibly sliding telescoping arrangement with each other. The first housing contains an active agent delivery chamber with an active agent formulation and a first expansion agent. The active agent formulation comprises at least one active agent. An open end in the first housing provides for delivery of the active agent formulation to the environment of use. The second housing contains an expansion chamber for separating apart the first and second housings of the device after exposure to the environment of use. The expansion chamber comprises a second expansion agent and optionally a piston. The first expansion agent within the first housing ensures essentially complete release of the active agent formulation to the environment of use.

The invention is also directed to a method for delivering essentially all of an active agent formulation to an environment of use following an initial period of delay. The method comprises placing the dispensing device of the invention into the environment of use, allowing fluid to be imbibed through at least a portion of the second housing of the dispensing device for causing the second expansion agent to expand over time and exert pressure on the slidably connected first and second housings. This pushes apart and separates the two housings of the device and exposes the active agent formulation of the first housing to the environment. Fluid enters the first housing, causing the first expansion agent to expand and push any remaining active agent formulation from the delivery device. Essentially all of the active agent is thus delivered into the environment of use.

DESCRIPTION OF THE DRAWINGS

The drawings are not drawn to scale, but are set forth to illustrate various embodiments of the invention. Like numbers refer to like structures.

DETAILED DESCRIPTION OF THE INVENTION

Figure 1:
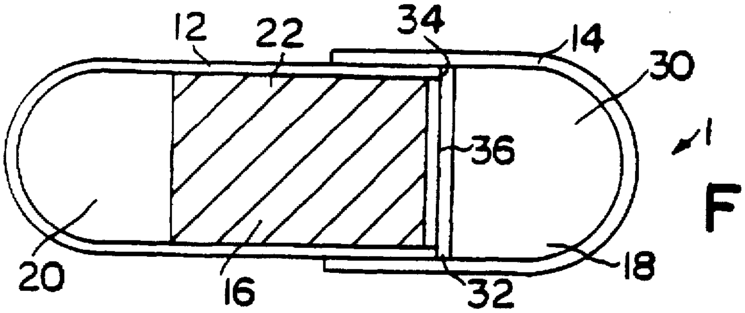
FIG. 1 is a side-elevational view of one embodiment of the delivery device of the present invention, the device being in closed or prepared form prior to placement in the environment of use.

The present invention provides a device which is useful for delivering an active agent formulation to a fluid environment of use. There is an initial delay period to startup or activation of the device, this delay period lasts a predetermined length of time, and is followed by essentially complete delivery of the active agent formulation to the environment of use.

DEFINITIONS

The phrase "initial delay period" intends a period of about a few minutes to a period of about a day, preferably between about 1 and 24 hours, and in particular between about 2 and 15 hours and usually in the range of about 4 to 7 hours. The delivery of the agent formulation from the dispensing device, once begun, is continued until essentially all of the active agent formulation is dispensed. By "essentially all of the active agent formulation" is intended at least about 95% of the active agent formulation, preferably above about 97% and usually greater than 98% of the active agent is delivered to the fluid environment of use. The active agent formulation is preferably administered as a bolus, i.e., the dose of active agent in the device is released in a short period of time of one hour or less and usually within about 30 minutes preferably within about 15 minutes of initiation of delivery of the active agent formulation.

By "semipermeable" is intended a material that is permeable to fluid but impermeable to other ingredients contained in the dispensing device. By "impermeable" is meant that the material is impermeable to fluids as well as to other ingredients contained in the dispensing device.

The term "active agent formulation" intends the drug or active agent optionally in combination with pharmaceutically acceptable carriers and additional inert ingredients. It is to be understood that more than one active agent may be incorporated into the active agent formulation in a device of this invention, and that the use of the term "agent" or "drug" in no way excludes the use of two or more such agents or drugs. The agents can be in various forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The terms "active agent" and "drug" are used interchangeably herein and refer to an agent, drug, compound, composition of matter or mixture thereof which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial agents useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, pednisolone, 17-β-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

As used herein, the terms "therapeutically effective" amount or rate refer to the amount or rate of the active agent needed to effect the desired therapeutic, often beneficial, result.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

FIG. 1 depicts, in side-elevational view, an embodiment of the delivery device according to the present invention. The device is shown in closed or prepared form prior to placement in the environment of use. Dispensing device 1 comprises a first housing 12 and a second housing 14. First housing 12 and second housing 14 are in slidably telescoping arrangement with each other. First housing 12 surrounds and defines an active agent delivery chamber 16 and contains a first expansion agent 20 and an active agent formulation 22.

Second housing 14 encompasses an expansion chamber 18 and contains a second expansion agent 30 and a moveable impermeable piston 32. Piston 32 is positioned between second expansion agent 30 and the open end 36 of first housing 12 which, when exposed to the environment, permits delivery of the active agent formulation to the environment of use.

First housing 12 and second housing 14 at their ends are close in size so that a friction fit is formed between the housings. The friction generated is sufficient to maintain the two housings together prior to activation of the second expansion agent 30 but not so great as to keep the two housings from sliding apart once an expanding driving force is exerted. The end of first housing 12 is adapted to fit within second housing 14. The bottom edge of the end of first housing 12 provides a platform or ridge 34. Ridge 34 is adapted to receive the driving force of second expansion agent 30, via piston 32, to separate the two housings.

In operation, dispensing device 1 is placed in the fluid environment of use and second expansion agent 30 begins to imbibe and absorb fluid through second housing 14 from the environment. Second expansion agent 30 expands, exerting a driving force via piston 32 against end or ridge 34 of first housing 12 to begin to slidably separate first housing 12 from second housing 14. First housing 12 and second housing 14 separate by the action of second expansion agent 30, via piston 32, on first housing ridge 34. In this manner, the open end of the first housing 12 is exposed to the fluid environment, and active agent formulation 22 delivery begins. During release of the active agent, fluid from the environment of use enters the open end 36 of first housing 12, thus causing first expansion agent 20 to imbibe fluid. As first expansion agent 20 imbibes fluid, it expands and pushes against active agent formulation 22. Agent formulation 22 therefore continues to be expelled from active agent delivery chamber 16 into the environment of use. The expansion agent 20 continues to expand and deliver active agent until the expansion agent 20 reaches the open end 36 of the first housing 12. At that point, which is within an hour, preferably within about 30 minutes and usually within about 15 minutes of the separation of the two housings, essentially all of the active agent formulation 22 has been delivered.

Figure 2:
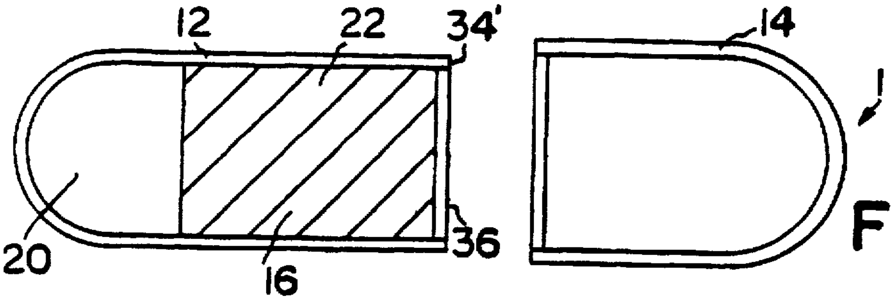
FIG. 2 shows the device of FIG. 1 in operation after placement in the environment of use, showing the second expansion means expanded and the first and second housings of the device separated to allow activation of the first expansion means to begin delivery of the active agent formulation to the environment.

FIG. 2 shows the dispensing device 1 of FIG. 1 in operation after separation of the two housings of the device. First housing 12 has been separated from second housing 14 by the expanding driving force of the second expansion agent 30, which has expanded in size as a result of imbibing fluid from the environment. The open end 36 of the first housing 12 is now exposed to the environment so that the active agent can be delivered.

Figure 3:
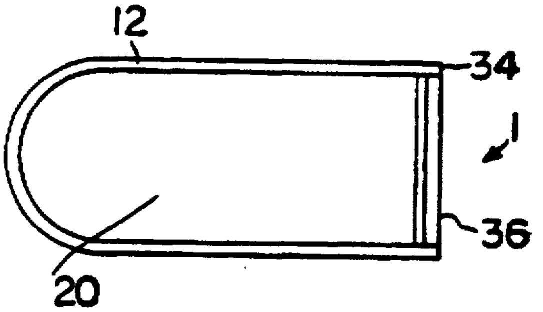
FIG. 3 shows the first housing of the device of FIG. 1 in operation at the end of its useful life, with the first expansion means expanded and the active agent formulation delivered to the environment.

FIG. 3 shows first housing 12 and the active agent delivery chamber 16 of dispensing device 1 of FIG. 1 after essentially all of the active agent has been delivered to the environment. First expansion agent 20 has expanded in size as a result of imbibing fluid from the open end 36 of first housing 12 to push active agent formulation 22 out of the first housing 12.

Figure 4:
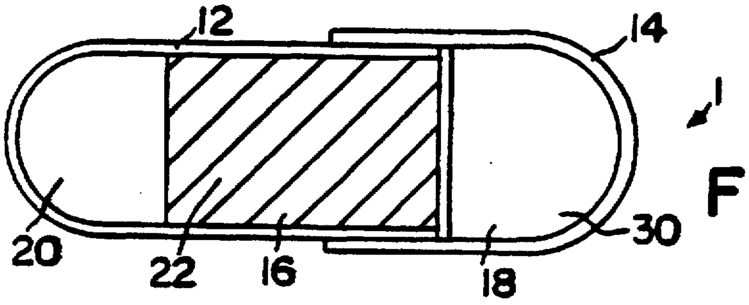
FIG. 4 is a side-elevational view of a further embodiment of the delivery device of the present invention, the device being in closed or prepared form prior to placement in the environment of use.

FIG.4 shows, in side-elevational view, a further embodiment of the delivery device according to the present invention. In this embodiment, the piston 32 shown in FIGS. 1–3 has been omitted and the expansion agent 30 pushes directly against active agent formulation 22 to accomplish separation of housings 12 and 14.

Figure 5:
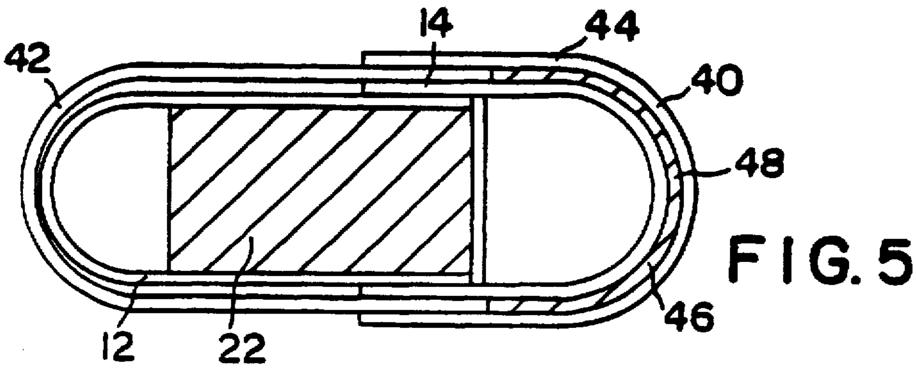
FIG. 5 is a side-elevational view of yet another embodiment of the delivery device of the present invention, the device being in closed or prepared form prior to placement in the environment of use.

FIG.5 shows, in side-elevational view, yet another embodiment of the delivery device according to the present invention. This embodiment is similar to the devices described above. A third housing 40, comprised of a first section 42 and a second section 44, defines a second active agent delivery chamber 46. The active agent formulation 48 contained within the delivery chamber 46 may be the same as the active agent formulation 22 or may be different. The active agent itself may be the same or it may be different. The housing may be comprised of a dissolvable material such as a gelatin capsule so that when introduced into the fluid environment, the housing 40 will dissolve and active agent formulation 48 will be released as a loading dose. Fluid will then be absorbed through housing 14 to effect separation of housing 12 and housing 14 and delivery of active agent formulation 22 as described above with regard to FIG. 1.

Because first expansion agent 20 operates by imbibing fluid that enters the open end 36 of the first housing 12 only after housings 12 and 14 have separated, the wall of first housing 12 is preferably comprised of an impermeable material in at least the portion of the housing that is in contact with the first expansion agent 20. In this way, the first expansion agent 20 is not prematurely activated prior to separation of the two housings of the device. When an active agent or an active agent dosage form is sensitive to fluid from an exterior fluid present in the environment of use, it is preferred that first housing 12 be substantially impermeable in its entirety to the ingress of the external fluid to serve as a means for substantially protecting the active agent formulation 22 as well as the first expansion agent 20.

Because second expansion agent 30 operates by imbibing external fluid while the housings 12 and 14 remain telescopically connected, the wall of second housing 14 in at least the portion that is adjacent to second expansion agent 30 must be semipermeable.

The walls of housings 12 and 14 optionally comprise additional ingredients such as, for example, a plasticizer. Impermeable and semipermeable compositions suitable for use in housings 12 and 14, as well as suitable additives, are known in the art, examples of which are disclosed in U.S. Pat. No. 4,874,388, which is incorporated herein by reference.

The delivery device of the present invention is nontoxic, biologically inert, nonallergenic and nonirritating to body tissue, and it maintains its physical and chemical integrity; that is, the device does not erode or degrade in the environment of use during the dispensing period. It is within the scope of the invention that the device be insoluble only during the period of intended use and can thereafter dissolve away in the environment of use. Thus, a dispenser is contemplated which is unaffected by its environment, solubility-wise, at the situs of use or which, alternatively, is only slightly soluble during the period of intended use, such that once its active agent content has been removed it will then dissolve or erode away.

The first and second expansion agents or expandable driving agents 20 and 30 are nontoxic, nonallergenic and biologically inert. Expansion agents 20 and 30 may be the same or they may be different. In one presently preferred embodiment, agents 20 and/or 30 comprise an osmopolymer. Osmopolymers interact with water and aqueous biological fluids and swell or expand to an equilibrium state. Osmopolymers exhibit the ability to swell in fluid and to retain a significant portion of the imbibed and absorbed fluid within the polymer structure. The expansion agents 20 and/or 30 in another preferred embodiment comprise an osmagent. Osmagents are also known as osmotically effective solutes and compounds. Osmagents that can be used for the purpose of this invention include inorganic and organic compounds that exhibit an osmotic pressure gradient across a semipermeable, i.e. a fluid-permeable wall. The expansion agents 20 and/or 30 in yet another preferred embodiment comprise an osmagent dispersed within an osmopolymer. The expansion agents can be in tablet or layer form, or can be a plurality of tablets or layers. The osmagent or osmopolymer can be in any suitable form such as particles, crystals, pellets, granules, porous hydrogels, elastic polymeric sponges and the like. Osmagents and osmopolymers are known to the art and are described in, for example, U.S. Pat. Nos. 3,865,108, 4,002,173, 4,207,893, 4,327,725 and 4,612,008 which are incorporated by reference herein.

Piston 32 may comprise a composition that is substantially impermeable to the passage of fluid and that restricts passage of fluid present in the expansion agent into the first housing. It operates to essentially maintain the integrity of the active agent formulation 22 and the expansion layer. Additionally, and importantly, piston 32 insures that the expanding driving force generated by the second expansion agent 30 is applied directly against first housing 12 to separate the first and second housings. Thus, piston 32 must be of sufficient strength, thickness and rigidity to transfer the driving force against first housing 12. Representative impermeable materials useful as piston 32 are known to the art and described in, for example, U.S. Pat. No. 4,874,388 which is incorporated herein by reference.

The active agent formulation comprises the active agent to be delivered, as a liquid, solid, semisolid or thermosensitive composition, generally in a carrier substance and with or without additional inert ingredients. The active agent formulation may additionally include dosage forms comprising the active agent that are capable of maintaining their physical configuration and chemical integrity while housed within the dispenser. These include, without limitation, tablets with or without a density element; matrix tablets; spheres; pellets and elongated tablets; capsules; elementary osmotic pumps, such as those described in U.S. Pat. No. 3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all of which patents are incorporated herein by reference.

The pharmaceutically acceptable carrier may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptible to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874 which is incorporated by reference herein. In a further embodiment, the formulation may include an osmotic agent or solute, such as those described above with reference to the expansion means, so that when the formulation comes into contact with the environmental fluid, it immediately dissolves. In yet another embodiment, the agent formulation can be comprised of an agent and a thermoresponsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermoresponsive" as used herein denotes the physical-chemical property of an agent carrier composition to exhibit solid, or solid-like properties at temperatures up to 31° C. and become fluid, semi-solid or viscous when disturbed by heat at temperatures from 31° C., usually in the range of 31° C. to 45° C. Suitable materials useful as active agent carriers and excipients are known in the art and are disclosed, for example, in U.S. Pat. Nos. 4,595,583 and 4,874,388, which are incorporated by reference herein.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

For proper delivery of the active agent, it may be desirable in some instances for the dispensing device to deliver active agent to a particular environment of use. Thus, it may be necessary for the device to remain in a particular environment of use until such time as the agent formulation has been delivered or, alternatively, for the device to pass through one particular environment to another prior to delivering agent formulation. In such cases, additional elements are included in the device, or the device is designed in such a way to provide for such particular delivery. For example, when the environment of use is the rumen of a ruminant animal, a density element may be included in the dispensing device so that the device is weighted to remain within the rumen during the dispensing period. Density elements are known in the art and are discussed in, for example, U.S. Pat. No. 4,874,388 which is incorporated by reference herein. When the environment of use is the human stomach, it may be desirable for the device to, for example, have a low initial density or to include air in that portion of the internal compartment of the device that also contains the agent formulation. In this manner, the device will float on the surface of the stomach contents and remain in the stomach until the device opens to release the formulation. Where it is desirable, on the other hand, to delay the release of an active agent which, for example, is inactivated by the stomach contents or may cause nausea or bleeding by irritating the gastric mucosa so that delivery in the stomach is not desired, an enteric coating can be applied over at least that portion of the housing of the dispensing device that is comprised of a semipermeable membrane. Enteric coatings will remain intact in the stomach but will rapidly dissolve once they arrive at the small intestine, thereafter allowing fluid to be imbibed to activate the dispensing device. Enteric coatings are well known in the art and are discussed in, for example, "Remington's Pharmaceutical Sciences", Mack Publishing Co., Easton, Pa.

The total delay time prior to separation of the two housings of the dispensing device and the total delivery time of the active agent formulation can be controlled by a number of means to provide a sharp start-up of delivery at a particular time with high accuracy. For example, the rate of fluid imbibition into each of the expansion means, and thus the rate of expansion of the means, can be controlled by the particular choice of semipermeable membrane or microporous screen. The rate of expansion of the expansion means can also be controlled by the choice of composition of the expansion means. The distance of overlap between the telescoping portions of the first and second housings can determine the period of time required for the two housings to separate. Combinations of such control means may be used. Such control means are known in the art and can be determined without undue experimentation.

The delivery device of the present invention can be manufactured by standard manufacturing techniques. For example, in the preparation of devices of the present invention, first housing 12 (the vessel) and second housing 14 (the cap) may be separately molded or extruded to the desired shape. Possible semipermeable materials from which the second housing 14 may be prepared include, for example, Hytrel® polyester elastomers (Du Pont), cellulose esters, water flux enhanced ethylene-vinyl acetate copolymers, semipermeable membranes made by blending a rigid polymer with water-soluble low molecular weight compounds, and other semipermeable materials known to the art. Impermeable materials from which the first housing 12 may be prepared include, for example, polyethylene, polystyrene, ethylene-vinyl acetate copolymers, Hytrel® polyester elastomers (Du Pont) and other impermeable materials known to the art. Alternatively, the two portions of a hard gelatin capsule may be coated, one with an impermeable material and the other with a semipermeable material such as cellulose ester-based polymer mixtures. In a presently preferred embodiment, the assembled device in closed configuration is about the size and dimensions of a size "O" to size "OO" hard gelatin capsule.

Expansion agent 20 is prepared from an osmotic material and formed into a shape that will fit within vessel 12. The layer is compressed into a tablet on a rotary bilayer tablet press. Expansion agent 30 is prepared from an osmotic material and piston 32 is prepared from an impermeable material. Both are formed into a shape that will fit within cap 14, and compressed on a bilayer rotary tablet press.

With reference to FIG. 1, the device is assembled as follows. Expansion agent 20 is inserted into the vessel 12 at its end opposite its open end 36. Active agent formulation 22 is then placed on top of expansion agent 20. The formulation may be in the from of a liquid, solid, semi-solid, powder or shaped tablet or tablets, for example. The expansion agent 30 and piston 32 are placed within the cap 14 and the cap assembly is placed over the end of the filled vessel 12 so that piston 32 is adjacent to the open end of the filled vessel 12.

The following examples are illustrative of the present invention. They are not to be construed as a limitation of the scope of the invention. Variations and equivalents of these examples will be apparent to one skilled in the art in light of the present disclosure, the drawings and the claims herein.

EXAMPLE 1

A delivery device according to the present invention for delivering progesterone into the colon for hormone replacement therapy is prepared as follows:

100 mg of Crosspovidone XL-10 (International Specialty Products, Wayne N.J.) powder was compressed in a rotary press into a cylindrical tablet to form the first expanding layer portion of the device. One face of the tablet was convex to conform to the shape of the device, while the other face is flat.

The second expanding layer portion of the device was formed from an osmotic layer and a barrier layer. The osmotic layer was formed as follows. Sodium chloride (NaCl) was sized and screened using a Quardo Mill with a 21 mesh screen at the speed set on maximum. This dry component was added to a granulator bowl of a Glatt fluid bed granulator with other dry components in the following proportions: 58.75 wt % sodium carboxymethyl cellulose (NaCMC), 30 wt % NaCl (prepared as described above), 5.0 wt % hydroxypropylmethyl cellulose E-5 (Aqualon), and 1.0 wt % red ferric oxide. The dry components were thoroughly mixed for 10 minutes. 5.0 wt % HPC-EF (Aqualon, Wilmington, DE) was dissolved in purified water and sprayed onto the dry components until the components were in granular form. Magnesium stearate (0.25 wt %) was then added to the granulation and the granulation was thoroughly mixed for 5 min.

The barrier layer part of the second expanding layer portion of the device was formed as follows. 95 wt % hydroxypropylmethyl cellulose E-5 (Aqualon) and 5.0 wt % stearic acid were sized and screened using a 40 mesh screen. The screened materials were added to a mixing vessel of a Hobart mixer and blended for 10 min. Ethanol was then slowly added while mixing until a wet mass was formed. The wet mass was then screened through a 20 mesh screen and the wet granules were allowed to air dry for 12 hours. After drying, the granules were again passed through a 20 mesh screen.

To form the second expanding layer portion of the device, osmotic layer granules (200 mg) and the barrier layer granules (50 mg) were compressed together in a rotary press into a cylindrical bilayer tablet with the osmotic layer face being convex and the barrier layer face being flat. Tabletting produced a clean, distinct interface between the two layers.

The drug layer portion of the device contained 80 wt % progesterone, 10 wt % Crosspovidone XL-10 (International Specialty Products, Wayne N.J.) and 9.5 wt % polyoxyethylene 40 stearate (ICI America International, Wilmington, Del.). During preparation, each of the components was screened through a 40 mesh screen and the sized components were added to a mixing vessel in the appropriate proportions. The dry components were mixed thoroughly until a wet mass was formed. The wet mass was then screened through a 20 mesh screen and the granules were oven-dried at 40° C. for 24 hours. After drying, the granules were passed through a 20 mesh screen. Magnesium stearate (0.5 wt %) was then added to the granulation and the granulation was mixed thoroughly for 5 min. The drug layer granules (125 mg) comprising 100 mg progesterone were then compressed in a rotary press into a cylindrical tablet with the top and bottom faces being flat.

The first housing (drug vessel), with one closed end and one open end, and composed of ethylene vinyl acetate copolymer (9 wt % vinyl acetate), was prepared by placing the pelletized ethylene vinyl acetate copolymer (EVA) in an extruder with a barrel temperature of 130° C. and extruding the material into a mold for the vessel. The EVA was allowed to cool in the mold, after which the finished vessel was removed.

A clear, size O gelatin capsule was used to form the second housing (engine assembly) of the device. The second expanding layer portion of the device was placed into the shorter segment of the capsule, the convex end of the tablet pointing into the closed end of the capsule. Polyvinylpyrrolidone (PVP k29-32, International Specialty Products) was dissolved in methanol and sprayed onto the capsule as a 2 mg subcoating. 75 wt % cellulose acetate 398-10 (Eastman Chemical, Kingsport, N.J.) and 25 wt % polyethylene glycol 3350 (Union Carbide, Danbury, CT) were dissolved in an acetone/methanol (80/20 wt/wt) solution to make a 4 wt % solid solution. This solution was sprayed onto the subcoating to form a 70 mg semipermeable membrane. The second housing was dried at 50° C. and 50%RH for 72 hours and then at 50° C. and ambient RH for 24 hours to anneal the coating and remove the residue solvents.

To assemble the delivery device, the first expanding layer portion of the device was placed into the first housing with the convex face of the tablet pointing into the closed end of the housing. The drug layer was then placed on top of the first expanding layer. The open end of this first housing was fitted into the open end of the second housing and the two housings were compressed together until the first housing, second expanding layer portion and second housing fit together tightly.

Figure 6:
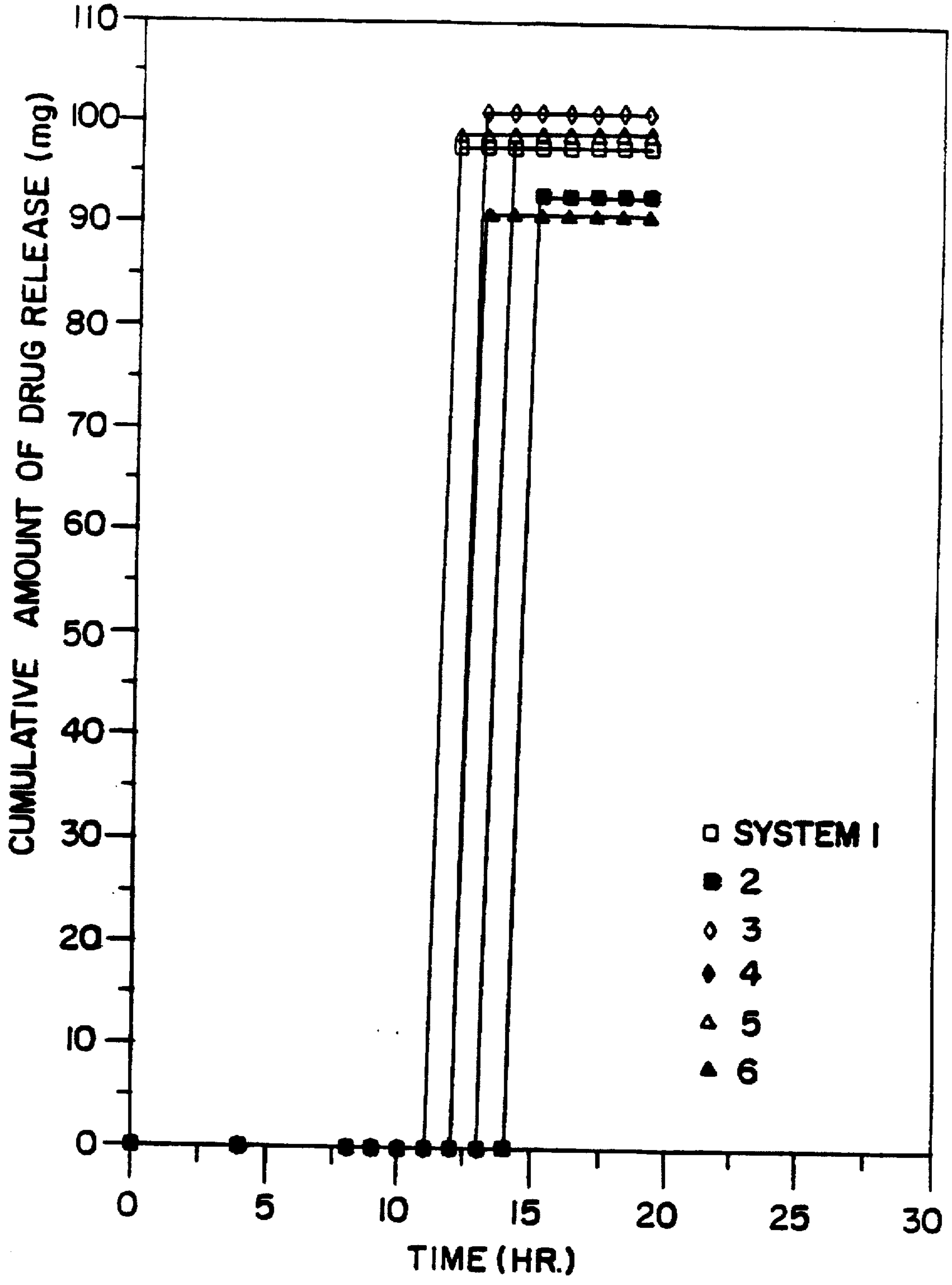
FIG. 6 is a graph showing the release characteristics of 5 inventive devices.

The opening times of the devices is shown in FIG. 6. The systems were placed in artificial gastric fluid (pH 1.4) for 2 hours, then, in artificial intestinal fluid for 22 hours. The opening times were determined to be the time interval at which the osmotic caps separated from the drug-containing vessels. The progesterone concentration was measured by HPLC following solubilization with ethanol. FIG. 6 shows the progesterone release profiles of six devices, indicated that the opening times were between 11 and 14 hours and the delivery was complete within 1 hour of the opening time.

EXAMPLE 2

A tablet containing 100 mg progesterone was encased in a #2 size gelatin capsule and administered with the device according to Example 1. The capsule will disintegrate and deliver the initial 100 mg of progesterone immediately upon administration and the remaining 100 mg will be administered 13 hours later.

EXAMPLE 3

A delivery device according to the present invention for delivering human growth hormone into the colon is prepared as follows:

90 mg of Crosspovidone XL-10 (International Specialty Products) powder was compressed in a rotary press into a cylindrical tablet to form the first expanding layer portion of the device. One face of the tablet was convex to conform to the shape of the device, while the other face is flat.

The second expanding layer portion of the device was formed from an osmotic layer and a barrier layer. The osmotic layer was formed as follows. Sodium chloride (NaCl) was sized and screened using a Quardo Mill with a 21 mesh screen at the speed set on maximum. This dry component was added to a granulator bowl of a Glatt fluid bed granulator with other dry components in the following proportions: 58.75 wt % sodium carboxymethyl cellulose (NaCMC), 30 wt % NaCl (prepared as described above), 5.0 wt % hydroxypropylmethyl cellulose E-5 (Aqualon), and 1.0 wt % red ferric oxide. The dry components were thoroughly mixed for 10 minutes. 5.0 wt % HPC-EF (Aqualon) was dissolved in purified water and sprayed onto the dry components until the components were in granular form. Magnesium stearate (0.25 wt %) was then added to the granulation and the granulation was thoroughly mixed for 5 min.

The barrier layer part of the second expanding layer portion of the device was formed as follows. 95 wt % hydroxypropylmethyl cellulose E-5 (Aqualon) and 5.0 wt % stearic acid were sized and screened using a 40 mesh screen. The screened materials were added to a mixing vessel of a Hobart mixer and blended for 10 min. Ethanol was then slowly added while mixing until a wet mass was formed. The wet mass was then screened through a 20 mesh screen and the wet granules were allowed to air dry for 12 hours. After drying, the granules were again passed through a 20 mesh screen.

To form the second expanding layer portion of the device, osmotic layer granules (250 mg) and the barrier layer granules (50 mg) were compressed together in a rotary press into a cylindrical bilayer tablet with the osmotic layer face being convex and the barrier layer face being flat. Tabletting produced a clean, distinct interface between the two layers.

The drug layer portion of the device contains 6.67 wt % recombinant human growth hormone (HGH) (ARES-Serono, Norwell, Md.), 78.33 wt % sodium salicylate (Bryant Lab, Berkeley, Calif.) and 15 wt % corn oil (Spectrum Chemical, Gardena, Calif.). During preparation, the sodium salicylate and HGH were each screened through an 80 mesh screen. The sized components were dry-blended for 15 minutes. The corn oil was added dropwise and mixed until homogeous. The oily mass was then screened through a 40 mesh screen to become granules. The drug layer granules (216 mg) were then compressed in a rotary press into a cylindrical tablet with the top and bottom faces being flat.

The first housing (drug vessel), with one closed end and one open end and composed of ethylene vinyl acetate copolymer (9 wt % vinyl acetate), was prepared by placing the pelletized ethylene vinyl acetate copolymer (EVA) in an extruder with a barrel temperature of 130° C. and extruding the material into a mold for the vessel. The EVA is allowed to cool in the mold, after which the finished vessel was removed.

A clear, size O gelatin capsule was used to form the second housing (engine assembly) of the device. The second expanding layer portion of the device was placed into the shorter segment of the capsule, the convex end of the tablet pointing into the closed end of the capsule. 90 wt % cellulose acetate 398-10 (Eastman Chemical, Kingsport, N.J.) and 10 wt % polyethylene glycol 3350 (Union Carbide, Danbury, Conn.) were dissolved in an acetone/methanol (80/20 wt/wt) solution to make a 4 wt % solid solution. This solution was sprayed onto the capsule to form a 29 mg semipermeable membrane. The second housing was dried at 50° C. and 50 %RH for 72 hours and then at 50° C. and ambient RH for 24 hours to anneal the coating and remove the residue solvents.

To assemble the delivery device, the first expanding layer portion of the device was placed into the first housing with the convex face of the tablet pointing into the closed end of the housing. The drug layer was then placed on top of the first expanding layer. The open end of this first housing was fitted into the open end of the second housing and the two housings were compressed together until the first housing, second expanding layer portion and second housing fit together tightly. The opening time of the system was measured as described in Example 1 and found to be about 6 hours. A dog transit study was conducted in which the devices were fed to dogs. The systems recovered from feces were assayed for the HGH formulation. The results of this study showed that 86% of the HGH formulation on average was delivered as compared to 62% for systems without the first expanding layer portion.

The above description has been given for ease of understanding only. No unnecessary limitations should be understood therefrom, as modifications will be obvious to those skilled in the art.

What is claimed is:

1. A fluid-imbibing delivery device for dispensing essentially all of an active agent formulation to a fluid environment of use after an initial, preset delay of startup of delivery, the device comprising:

(a) a first housing and a second housing, the first and second housings being in reversibly sliding telescoping arrangement with each other, the second housing having an open end and a closed end and being semipermeable;

(b) said first housing having an open end and a closed end, said open end of said first housing being slidably received in said open end of said second housing, and said first housing containing an active agent formulation located adjacent its open end and a biologically inert first expansion agent devoid of active agent formulation located adjacent its closed end, said active agent formulation and said first expansion agent being contained within said first housing; and (c) said second housing containing a second expansion agent, wherein said second expansion agent upon imbibing fluid operates to separate said first and second housings and said first expansion agent upon imbibing fluid operates to dispense essentially all of said active agent formulation from said first housing.

2. The device of claim 1 wherein the first housing is impermeable.

3. The device of claim 1 wherein the first and second expansion agents are selected from the group consisting of osmagents, osmopolymers and mixtures thereof.

4. The device of claim 1 comprising a piston disposed between said second expansion agent and said active agent formulation.

5. The device of claim 1 wherein the active agent formulation comprises progesterone.

6. The device of claim 1 wherein the active agent formulation comprises human growth hormone.

7. The device of claim 1 wherein the active agent formulation is selected from the group consisting of liquid, solid, semi-solid, thermo-responsive formulations, and mixtures thereof.

8. The device of claim 1 further comprising a third housing surrounding said first and second housings.

9. The device of claim 1 that further comprises an enteric coating.

10. A fluid-imbibing delivery device for dispensing essentially all of an active agent formulation to a fluid environment of use after an initial, preset delay of startup of delivery, the device comprising:

(a) a first housing and a second housing, the first and second housings being in reversibly sliding telescoping arrangement with each other, the second housing having an open end and a closed end and being semipermeable;

(b) said first housing having an open end, and a closed end, said open end of said first housing being slidably received in said open end of said second housing, and said first housing containing an active agent formulation located adjacent its open end and a biologically inert first expansion agent devoid of active agent formulation located adjacent its closed end, said active agent formulation and said first expansion agent being contained within said first housing;

(c) said second housing containing a second expansion agent; and (d) a third housing containing a second active agent formulation comprising a second active agent, said third housing concentrically surrounding said first and second housings and being adapted to release the active agent formulation when placed in the environment of use and expose the second housing to a fluid environment;

wherein said second expansion agent upon imbibing fluid operates to separate said first and second housings and said first expansion agent upon imbibing fluid operates to dispense essentially all of said active agent formulation from said first housing.

11. The device of claim 10 wherein the first and second active agents are different.

12. The device of claim 10 wherein the first and second active agents are the same.

13. The device of claim 12 wherein the first and second active agents are progesterone.

14. The device of claim 10 wherein the first housing is impermeable.

15. The device of claim 10 that further comprises an enteric coating.

16. The device of claim 10 comprising a piston disposed between said second expansion agent and said active agent formulation.

* * * * *